US00PP09520P

United States Patent [19]

Trees

[11] Patent Number: Plant 9,520

[45] Date of Patent: Apr. 23, 1996

[54] NEW GUINEA IMPATIENS NAMED 'BFP-467 CHERRY RED'

[75] Inventor: Scott C. Trees, Arroyo Grande, Calif.

[73] Assignee: Geo. J. Ball, Inc., West Chicago, Ill.

[21] Appl. No.: 422,228

[22] Filed: Apr. 14, 1995

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—Burns, Doane, Swecker & Mathis

[57] ABSTRACT

A new and distinct New Guinea Impatiens cultivar named 'BFP-467 Cherry Red' is provided. This new cultivar was the result of a controlled breeding program wherein the 'BFP-364 Deep Coral' cultivar (U.S. Plant patent application Ser. No. 338,162, filed Nov. 8, 1994) was pollinated by a plant designated BFP-307 (non-patented in the United States). The new cultivar forms attractive large round cherry red flowers displaying an iridescent appearance, forms moderately dark green foliage, exhibits a good basal branching character, and exhibits a medium-vigorous upright growth habit. The new cultivar can be readily distinguished from the 'Martinique' cultivar (non-patented in the United States).

1 Drawing Sheet

SUMMARY OF THE INVENTION

The present invention provides a new and distinctive Impatients plant, botanically known as New Guinea Impatients, and hereinafter referred to by the cultivar name 'BFP-467 Cherry Red'.

The new cultivar is the product of a planned breeding program. More specifically, the breeding program which resulted in the production of the new cultivar was carried out in a controlled environment during 1992 at Arroyo Grande, Calif., U.S.A. The female parent (i.e., the seed parent) was the 'BFP-364 Deep Coral' cultivar (U.S. Plant patent application Ser. No. 338,162, filed Nov. 8, 1994) which exhibits dark coral flowers with variegated bronze foliage. The male parent (i.e., the pollen parent) was a plant designated BFP-307 (non-patented in the United States) which exhibits large red flowers and moderately dark green foliage. The parentage of the new cultivar can be summarized as follows:

'BSP-364 Deep Coral'×BFP 307.

The seeds resulting from the above pollination were sown and plantlets were obtained which were physically and biologically different from each other. Selective study resulted in the identification of a single plant of the new cultivar. This plant had large coral flowers and initially was designated BFP-467. Another progeny of the same cross named 'BFP-523 Deep Red' forms the subject matter of U.S. Plant patent application Ser. No. 08/422,231, filed concurrently herewith.

It was found that the new cultivar of the present invention:

(a) exhibits attractive large cherry red flowers, (b) forms moderately dark green foliage, (c) exhibits a good branching character, and (d) exhibits a medium-vigorous upright growth habit.

Asexual reproduction of the new cultivar by terminal or stem cuttings taken during 1993, at Arroyo Grande, Calif., U.S.A., has demonstrated that the characteristics of the new cultivar as herein described are firmly fixed and are retained through successive generations of such asexual propagation.

The 'BFP-467 Cherry Red' cultivar has not been observed under all possible environmental conditions to date. Accordingly, it is possible that the phenotype may vary somewhat with variations in the environment, such as temperature, light intensity, and day length.

When the new cultivar of the present invention is compared to the 'Martinque' cultivar (non-patented in the United States) it is found that the new variety exhibits larger flowers (e.g., approximately 6.0 to 6.7 cm×approximately 6.0 to 6.5 cm. vs. approximately 5.0 to 5.8 cm.×approximately 5.0 to 5.6 cm.), and larger leaves (e.g., approximately 10.5 to 11.0 cm.×approximately 3.7 to 4.2 cm. vs. approximately 9.0 to 9.6 cm.×approximately 3.1 to 3.7 cm.).

When plant material of the 'BFP-467 Cherry Red' cultivar is subjected to standard random amplified polymorphic DNA marker analysis (RAPD) using polymerase chain reaction (PCR) and a known unique set of DNA primers, it is found to exhibit a different fingerprint map when compared to that of 'Martinique' cultivar which confirms its genetic distinctiveness.

Plants of the new cultivar will be marketed under the CELEBRATION trademark by Geo. J. Ball, Inc.

BRIEF DESCRIPTION OF THE PHOTOGRAPH

The accompanying photograph of FIG. 1 shows as nearly true as it is reasonably possible to make the same in a color illustration of this character, a typical specimen of an overall plant of the new cultivar. Tyical flower and foliage characteristics are illustrated. The plant was grown in a greenhouse at West Chicago, Ill., U.S.A.

DETAILED DESCRIPTION

Figure 1:
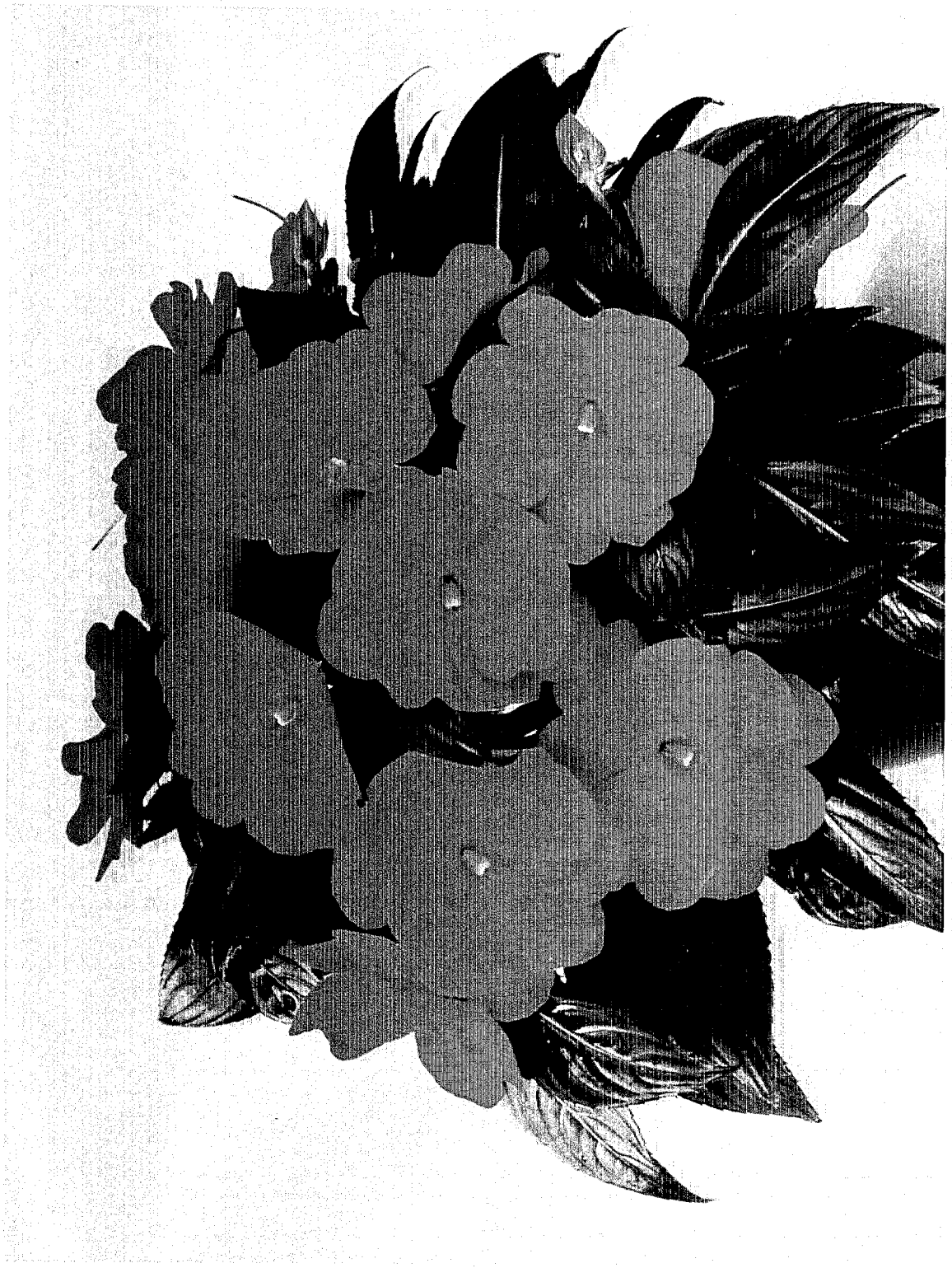

The chart used in the identification of colors described herein is the R.H.S. Colour Chart of The Royal Horticultural Society, London, England. The color values were determined on Jan. 3, 1995. The readings were taken between 1:00 and 1:45 p.m. under 2,000 footcandles of light at West Chicago, Ill., U.S.A. The plants were produced from cuttings taken from stock plants and were grown undergreenhouse conditions comparable to those used in commercial practice while utilizing a soilless growth medium and maintaining temperatures of approximately 72° F. during the day and approximately 65° F. during the night.

Propagation:

Type cutting.—Terminal tip.

*Time to initiate roots.*—Approximately 14 to 21 days with the shorter times generally being experienced in the summer and the longer times in the winter.

*Rooting habit.*—Fibrous, and branching.

Plant description:

*Habit of growth.*—Basal branching.

*Form.*—Medium-vigorous upright mounded. A mature plant commonly measures approximately 9 to 11 cm. in height and approximately 24 to 28 cm. in width compared to approximately 9 to 10 cm. in height and approximately 21 to 26 cm. in width for the 'Martinique' cultivar.

*Foliage.*—The configuration is narrow and lanceolate. The leaves of the new cultivar commonly measure approximately 10.5 to 11.0 cm. in length and approximately 3.7 to 4.2 cm. in width while those of the 'Martinique' cultivar commonly measure approximately 9.0 to 9.6 cm. in length and approximately 3.1 to 3.7 cm. in width. The foliage of the new cultivar is Green Group 137B (adaxial) and Green Group 138B (abaxial). This can be compared to Green Group 137A (adaxial) and Green Group 138B with a mid-rib of Red-Purple Group 59A (abaxial) for the 'Martinique' cultivar. The stem color is Green Group 143C with some Greyed-Purple Group 185A at the nodes. This can be compared to Greyed-Purple Group 185A for the 'Martinique' cultivar.

Flower description:

*Flowering habit.*—Freely flowering.

*Natural flowering season.*—Throughout the year in a greenhouse environment.

*Flowers borne.*—Above the foliage arising from leaf axils.

*Flower color.*—Red Group 46A (adaxial) and Red Group 46D (abaxial). This can be compared to Red Group 45A (adaxial) and Red Group 45C (abaxial) for the 'Martinique' cultivar.

Quantity of flowers.—Approximately 3 to 4 per stem compared to 3 to 4 per branch for the 'Martinique' cultivar.

*Number of petals.*—Five.

*Flower size.*—Approximately 6.0 to 6.7 cm. in length and approximately 6.0 to 6.5 cm. in width. This can be compared to a length of approximately 5.0 to 5.8 cm. and a width of approximately 5.0 to 5.6 cm. for the 'Martinique' cultivar.

*Nectary length.*—Approximately 4.9 to 5.5 cm. which can be compared to approximately 4.5 to 4.6 cm. for the 'Martinique' cultivar.

*Nectary color.*—Red Group 53C which can be compared to Red Group 51A for the 'Martinique' cultivar.

Reproductive organs.—The anthers are fused together forming one organ that surrounds the pistil. Generally the anthers shed pollen prior to the stigma becoming receptive. The pollen color is Yellow Group 11D. The stigma color is red-orange. The ovary color is Yellow-Green Group 144C for both the new cultivar and the 'BFP-467 Cherry Red' cultivar.

I claim:

1. A new and distinct cultivar of New Guinea Impatiens plant named 'BFP-467 Cherry Red' substantially as herein shown and described, which:

(a) exhibits attractive large cherry red flowers, (b) forms moderately dark green foliage, (c) exhibits a good basal branching character, and (d) exhibits a medium-vigorous upright growth habit.

* * * * *